United States Patent [19]
Gueli

[11] Patent Number: 5,916,088
[45] Date of Patent: Jun. 29, 1999

[54] COOLING BEACH PILLOW

[76] Inventor: Martin Gueli, 4075 Worcester Rd., Sarasota, Fla. 34231

[21] Appl. No.: 09/178,598

[22] Filed: Oct. 26, 1998

[51] Int. Cl.⁶ .................................. A47G 9/00; A61F 7/00
[52] U.S. Cl. .......................... 5/639; 5/644; 5/909; 5/636; 607/114; 224/616
[58] Field of Search ................ 5/639, 636, 644, 5/645, 909, 421; 224/616, 614; 607/114, 112, 109, 110

[56] References Cited

U.S. PATENT DOCUMENTS

| | | | |
|---|---|---|---|
| 4,116,310 | 9/1978 | Shields | 5/639 |
| 4,325,151 | 4/1982 | Wu | 5/644 |
| 4,847,931 | 7/1989 | Bard | 5/644 |
| 4,858,259 | 8/1989 | Simmons et al. | 5/644 |
| 4,887,326 | 12/1989 | O'Brien et al. | 5/644 |
| 4,896,388 | 1/1990 | Bard | 5/644 |
| 5,072,429 | 12/1991 | Mair | 5/639 |
| 5,344,437 | 9/1994 | Pistay | 5/639 |
| 5,545,199 | 8/1996 | Hudson | 5/644 |
| 5,632,051 | 5/1997 | Stanley et al. | 5/644 |

Primary Examiner—Alex Grosz

[57] ABSTRACT

The present invention is a pillow/headrest designed to keep a user cool and comfortable when sunbathing, using a tanning bed or reclining in any uncomfortably warm environment. The pillow system comprises a housing in a generally rectangular configuration having an upper surface and a lower surface with a front edge and a rear edge and side faces. A generally rectangular gel pocket is formed in the upper surface and is adapted to contain a layer of thermally conductive gel material. A slot is formed in the rear edge with a chamber for the removable receipt of a freezer pack of thermal material.

4 Claims, 3 Drawing Sheets

COOLING BEACH PILLOW

BACKGROUND OF THE INVENTION

1. Field of the Invention

The present invention relates to a new and improved beach pillow and, more particularly, pertains to keeping a user cool and comfortable while sunbathing, using a tanning bed or reclining in an uncomfortably warm environment.

2. Description of the Prior Art

The use of pillows and cooling devices of known designs and configurations is known in the prior art. More specifically, pillows and cooling devices of known designs and configurations heretofore devised and utilized for the purpose of keeping a person comfortable while in a reclining position through known methods and apparatuses are known to consist basically of familiar, expected, and obvious structural configurations, notwithstanding the myriad of designs encompassed by the crowded prior art which has been developed for the fulfillment of countless objectives and requirements.

The prior art discloses a large number of pillows and cooling devices of known designs and configurations. By way of example, U.S. Pat. No. 3,312,987 to Emery, issued Apr. 11, 1967 discloses a U-shaped pillow. U.S. Pat. No. 4,858,259 to Simmons et al., issued Aug. 22, 1989 discloses a therapy pillow with removable therapeutic pack. U.S. Pat. No. 4,887,326 to O'Brien et al., issued Dec. 19, 1989 discloses a suboccipital pillow. U.S. Pat. No. 5,344,437 to Pistay, issued Sep. 6, 1994 discloses a massaging therapeutic pillow with removable ice pack. Lastly, U.S. Pat. No. 5,545,199 to Hudson, issued Aug. 13, 1996 discloses a hot and cold therapeutic pillow. International Application WO 96/13186 to Stanley et al., issue/priority date May 9, 1996 discloses a cooling fluid container.

In this respect, the beach pillow according to the present invention substantially departs from the conventional concepts and designs of the prior art, and in doing so provides an apparatus primarily developed for the purpose of keeping a user cool and comfortable while sunbathing, using a tanning bed or reclining in an uncomfortably warm environment.

Therefore, it can be appreciated that there exists a continuing need for a new and improved beach pillow which can be used for keeping a user cool and comfortable while sunbathing, using a tanning bed or reclining in an uncomfortably warm environment. In this regard, the present invention substantially fulfills this need.

SUMMARY OF THE INVENTION

In view of the foregoing disadvantages inherent in the known types of pillows and cooling devices of known designs and configurations now present in the prior art, the present invention provides a new and improved beach pillow. As such, the general purpose of the present invention, which will be described subsequently in greater detail, is to provide a new and improved beach pillow and methods which have all the advantages of the prior art and none of the disadvantages.

To attain this, the present invention essentially comprises a new and improved beach pillow system to keep a user cool and comfortable while sunbathing, using a tanning bed or reclining in an uncomfortably warm environment comprising, in combination, a housing in a generally rectangular configuration having an upper surface and a lower surface with a narrow front edge and a thick rear edge and with-curved-side faces; a generally rectangular gel pocket formed in the upper surface adapted to contain a layer of thermally conductive gel material; a slot formed in the rear edge with a chamber for the removable receipt of a freezer pack of thermal material capable of being frozen in a freezer and placed into the chamber for providing a cooling effect to the gel pack and a user's head thereon; a quantity of thermal insulation within the chamber between the chamber and lower surface adapted to hold the pillow in its intended rectangular configuration; a generally rectangular recess formed in the lower surface adapted to conform to a user's head when placed thereon; a multi-function timer located within one side wall proximate to the rear edge thereof; a pair of button-like projections extending outwardly from the opposed side walls adjacent to the rear end thereof; and a strap having keyhole openings at its opposite ends adapted for releasably coupling to the projections extending from the side walls.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved beach pillow which has all the advantages of the prior art pillows and cooling devices of known designs and configurations and none of the disadvantages.

It is another object of the present invention to provide a new and improved beach pillow which may be easily and efficiently manufactured and marketed.

It is a further object of the present invention to provide a new and improved beach pillow which is of a durable and reliable construction.

An even further object of the present invention is to provide a new and improved beach pillow which is susceptible of a low cost of manufacture with regard to both materials and labor, and which accordingly is then susceptible of low prices of sale to the consuming public, thereby making such a beach pillow economically available to the buying public.

Even still another object of the present invention is to keep a user cool and comfortable while sunbathing, using a tanning bed or reclining in an uncomfortably warm environment.

Lastly, it is an object of the present invention to provide a pillow/headrest designed to keep a user cool and comfortable when sunbathing, using a tanning bed or reclining in any uncomfortably warm environment. The pillow system comprises a housing in a generally rectangular configuration having an upper surface and a lower surface with a front edge and a rear edge and side faces. A generally rectangular gel pocket is formed in the upper surface and is adapted to contain a layer of thermally conductive gel material. A slot is formed in the rear edge with a chamber for the removable receipt of a freezer pack of thermal material.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
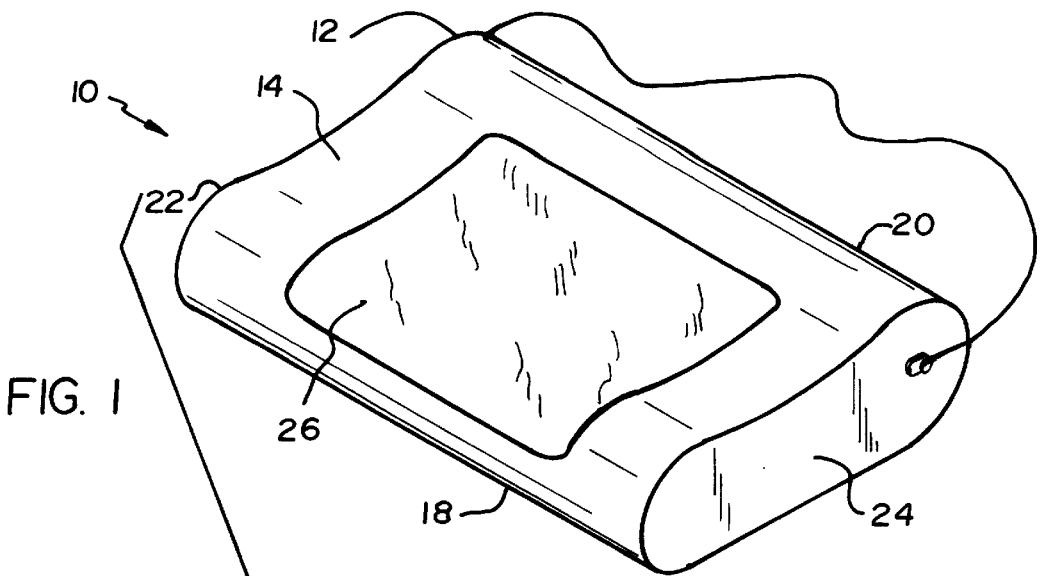
FIG. 1 is a perspective illustration of the new and improved beach pillow shown in combination with the removable freezer pack constructed in accordance with the principles of the present invention.

With reference now to the drawings, and in particular to FIGS. 1 through 5 thereof, the new and improved beach pillow embodying the principles and concepts of the present invention and generally designated by the reference numeral 10 will be described.

The present invention, the new and improved beach pillow, is a system 10 comprised of a plurality of components. Such components, in their broadest context, include a housing, a gel pocket, a slot and freezer pack chamber, a freezer pack, thermal insulation, a recess, a timer, projections and a strap. Each of the individual components is specifically configured and correlated one with respect to the other so as to attain the desired objectives.

The present invention includes a housing 12 in a generally rectangular configuration. The housing has an upper surface 14 and a lower surface 16 with a narrow front edge 18 and a thick rear edge 20 and side faces 22, 24.

Figure 2:
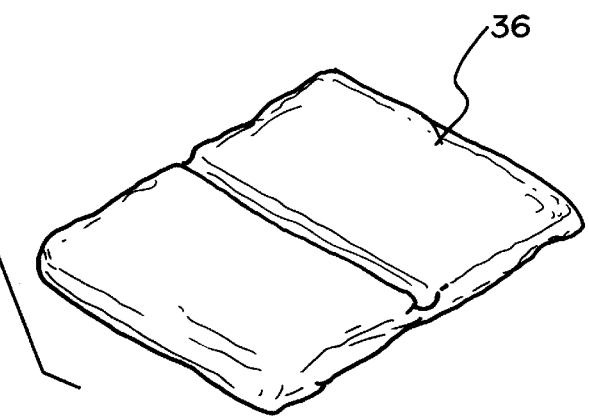
FIG. 2 is a cross-sectional view taken adjacent the rear edge thereof.
Figure 2:
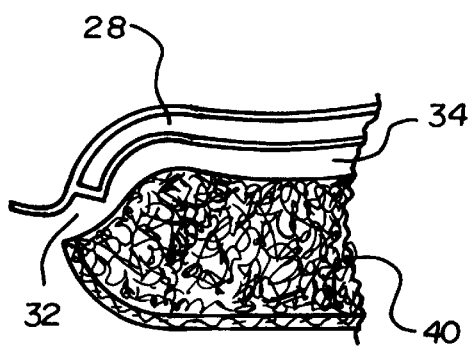
Figure 3:
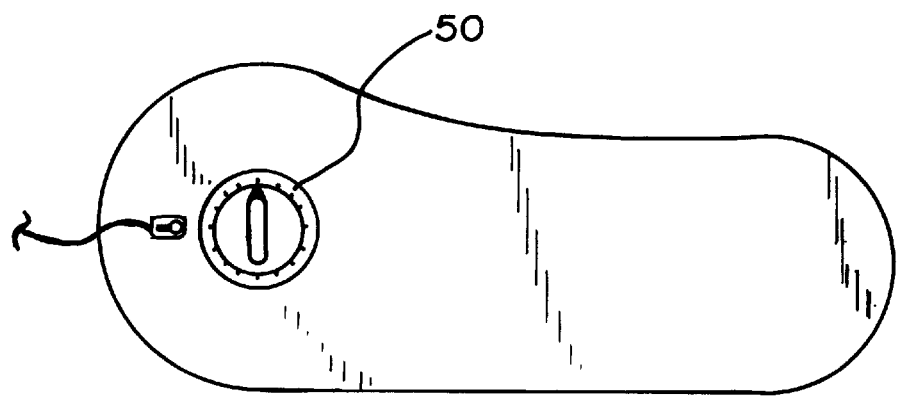
FIG. 3 is a side elevational view of one side edge of the device shown in FIG. 1, illustrating the multi-function timer.
Figure 4:
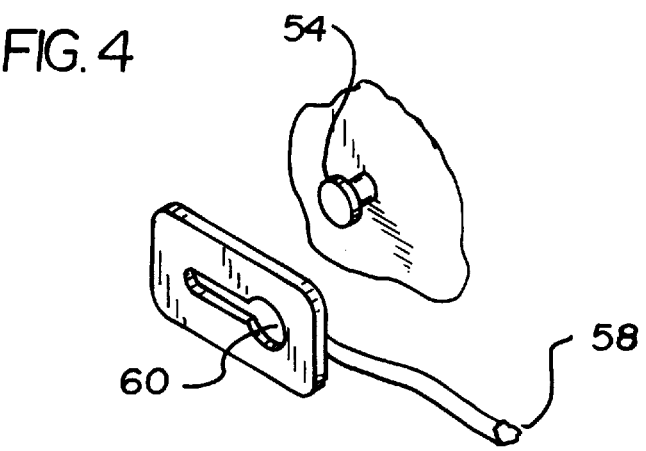
FIG. 4 is a perspective illustration of the button and coupling strap as shown in FIG. 1.
Figure 5:
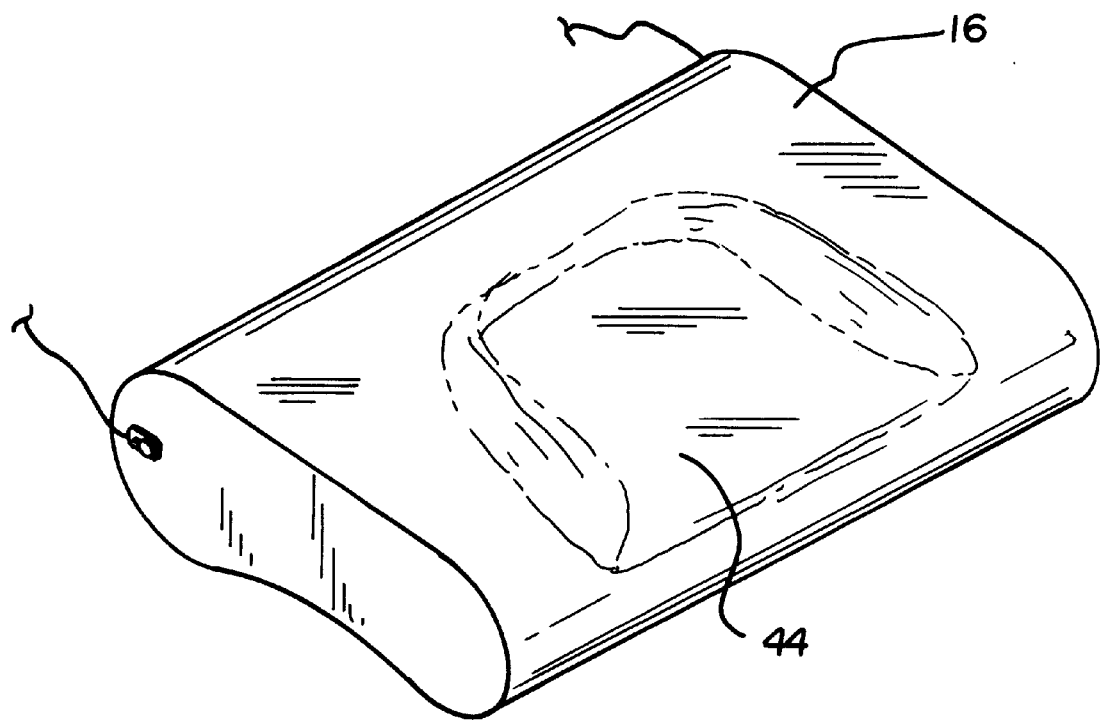
FIG. 5 is a perspective view of the bottom of the pillow as shown in FIG. 1.

Next provided is a generally rectangular gel pocket 26 partially designed by the upper surface adapted to contain a layer of thermally conductive gel material 28, as best seen in FIG. 2.

A slot 32 is formed in the rear edge with a chamber 34 for the removable receipt of a freezer pack 36 of thermal material capable of being frozen in a freezer and placed into the chamber for providing a cooling effect to the gel pack and a user's head thereon.

Further provided is a quantity of thermal insulation 40 within the chamber between the chamber and lower surface adapted to hold the pillow in its intended rectangular configuration.

Also provided is a generally rectangular recess 44 formed in the lower surface adapted to conform to a user's head when placed thereon.

Next provided is a multi-function timer 50 located within one side wall proximate the rear edge thereof.

Further provided is a pair of button-like projections 54 which extend outwardly from the opposed side walls adjacent to the rear edge thereof.

Lastly provided is a strap 58 having keyhole openings 60 at its opposite ends adapted for releasably coupling to the projections extending from the side walls.

The present invention is a pillow/headrest designed to keep the user cool and comfortable while sunbathing, using a tanning bed or reclining in any uncomfortably warm environment.

The present invention consists of a three-part device having an overall shape of a neck-cradling headrest. However, the back of the pillow opens up like a pocket to provide access to an interior compartment. This compartment is shaped to closely fit the provided freezer pack. Once inserted into the pillow, the freezer pack begins chilling the liquid gel-pack contained in the top of the pillow. This cold-conducting gel-pack provides a cool refreshing effect to the user's head and neck. The bottom section of the headrest compartment, underneath the freezer pack, is made of an insulating material, or is a plastic molded form that is filled with insulating material.

The present invention also features a timer with alarm that can be set to alert the user after a designated period of time has elapsed. This feature is useful in preventing UV overexposure or to signal the user to turn over to achieve an even tan. The timer unit could be inset within one side wall.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved beach pillow system to keep a user cool and comfortable while sunbathing, using a tanning bed or reclining in an uncomfortably warm environment comprising, in combination:

a housing in a generally rectangular configuration having an upper surface and a lower surface with a narrow front edge and a thick rear edge and with side faces;

a generally rectangular gel pocket partially defined by formed in the upper surface containing adapted to a layer of thermally conductive gel material;

a slot formed in the rear edge with a chamber removably containing of a freezer pack of thermal material capable of being frozen in a freezer and placed into the chamber for providing a cooling effect to the gel pack and a user's head thereon;

a quantity of thermal insulation within the chamber between the chamber and lower surface adapted to hold the pillow in its intended rectangular configuration.

2. The system as set forth in claim 1 and further including:

a generally rectangular recess formed in the lower surface adapted to conform to a user's head when placed thereon.

3. The system as set forth in claim 1 and further including:

a multi-function timer located within one side wall proximate to the rear edge thereof.

4. The system as set forth in claim 1 and further including:

a pair of button-like projections extending outwardly from the opposed side walls adjacent to the rear edge thereof; and a strap having keyhole openings at its opposite ends adapted for releasably coupling to the projections extending from the side walls.

* * * * *